United States Patent
Ohba et al.

(10) Patent No.: US 11,020,371 B2
(45) Date of Patent: Jun. 1, 2021

(54) ANTI-NOROVIRUS COMPOSITION AND UTILIZATION THEREOF

(71) Applicants: YAIZU SUISANKAGAKU INDUSTRY CO., LTD., Yaizu (JP); GENERAL INCORPORATED ASSOCIATION PHARMA VALLEY PROJECT SUPPORTING ORGANIZATION, Mishima (JP)

(72) Inventors: Mai Ohba, Shizuoka (JP); Takayuki Ando, Shizuoka (JP); Akira Asai, Shizuoka (JP); Naohisa Ogo, Shizuoka (JP)

(73) Assignees: YAIZU SUISANKAGAKU INDUSTRY CO., LTD., Yaizu (JP); GENERAL INCORPORATED ASSOCIATION PHARMAVALLEY PROJECT SUPPORTING ORGANIZATION, Mishima (JP)

( * ) Notice: Subject to any disclaimer, the term of this patent is extended or adjusted under 35 U.S.C. 154(b) by 0 days.

(21) Appl. No.: 16/065,430

(22) PCT Filed: Dec. 20, 2016

(86) PCT No.: PCT/JP2016/087863
§ 371 (c)(1),
(2) Date: Jun. 22, 2018

(87) PCT Pub. No.: WO2017/110767
PCT Pub. Date: Jun. 29, 2017

(65) Prior Publication Data
US 2019/0000796 A1 Jan. 3, 2019

(30) Foreign Application Priority Data
Dec. 25, 2015 (JP) .............................. JP2015-253661

(51) Int. Cl.
| | | |
|---|---|---|
| *A61K 31/352* | (2006.01) | |
| *A23L 33/105* | (2016.01) | |
| *A61K 31/045* | (2006.01) | |
| *A61K 36/82* | (2006.01) | |
| *A61K 9/00* | (2006.01) | |
| *A61K 9/08* | (2006.01) | |
| *A23G 1/00* | (2006.01) | |
| *A61L 2/00* | (2006.01) | |
| *A23G 3/48* | (2006.01) | |
| *A23G 4/06* | (2006.01) | |
| *A61K 9/68* | (2006.01) | |
| *A61K 47/10* | (2017.01) | |

(52) U.S. Cl.
CPC .......... *A61K 31/352* (2013.01); *A23G 1/0013* (2013.01); *A23G 1/0036* (2013.01); *A23G 1/0046* (2013.01); *A23G 1/0056* (2013.01); *A23G 3/48* (2013.01); *A23G 4/068* (2013.01); *A23L 33/105* (2016.08); *A61K 9/006* (2013.01); *A61K 9/0014* (2013.01); *A61K 9/0056* (2013.01); *A61K 9/0058* (2013.01); *A61K 9/08* (2013.01); *A61K 31/045* (2013.01); *A61K 36/82* (2013.01); *A61K 47/10* (2013.01); *A61L 2/0088* (2013.01); *A23V 2002/00* (2013.01)

(58) Field of Classification Search
CPC .... A61K 31/045; A61K 31/352; A61K 36/82; A61K 47/10; A61K 9/0014; A61K 9/0056; A61K 9/0058; A61K 9/006; A61K 9/08; A23G 1/0013; A23G 1/0036; A23G 1/0046; A23G 1/0056; A23G 3/48; A23G 4/068; A23L 33/105; A23V 2002/00; A61L 2/0088; A61P 31/12; A61P 31/14; A61P 43/00
See application file for complete search history.

(56) References Cited

U.S. PATENT DOCUMENTS

2012/0129950 A1* 5/2012 Macinga ................ A01N 31/02
514/738

FOREIGN PATENT DOCUMENTS

| JP | 54-20520 B1 | 7/1979 |
|---|---|---|
| JP | 7-148407 A | 6/1995 |
| JP | 5092145 B2 | 12/2012 |
| JP | 2014-12715 A | 1/2014 |
| JP | 2014-19659 A | 2/2014 |
| JP | 2015-171323 A | 10/2015 |

OTHER PUBLICATIONS

Oh et al. (2013, Food Sci. Biotechnol. 22(2), pp. 593-598) (Year: 2016).*
Friedman et al. (2006, Journal of Food Science, vol. 71, No. 6, pp. 0328-0337). (Year: 2006).*
International Preliminary Report on Patentability with a Translation of Written Opinion issued from the International Bureau in counterpart International Application No. PCT/JP2016/087863, dated Jun. 26, 2018.
Atsushi Mukoyama, et al., "Inhibition of Rotavirus and Enterovirus Infections by Tea Extracts", Jpn.J.Med.Sci.Biol., 1991, pp. 181-186, vol. 44, No. 4.
K.J. Clark, et al., "An in vitro study of theaflavins extracted from black tea to neutralize bovine rotavirus and bovine coronavirus infections", Veterinary Microbiology, 1998, pp. 147-157, vol. 63, No. 2-4.

(Continued)

*Primary Examiner* — Kara R McMillian
(74) *Attorney, Agent, or Firm* — Sughrue Mion, PLLC (57) ABSTRACT

Provided are: a composition having an excellent anti-norovirus effect; use of a theaflavin compound for the preparation of the composition; and a method for preventing infection with a norovirus using a theaflavin compound. A theaflavin compound is used as an active ingredient for preventing infection with a norovirus. The theaflavin compound is preferably used together with an alcohol. The theaflavin compound is preferably one or more members selected from the group consisting of theaflavin, theaflavin-3-O-gallate, theaflavin-3'-O-gallate and theaflavin-3,3'-O-digallate that are derived from tea components.

4 Claims, 3 Drawing Sheets

(56) References Cited

OTHER PUBLICATIONS

Charles E. Isaacs, et al., "Digallate Dimers of (-)-Epigallocatechin Gallate Inactivate Herpes Simplex Virus", Antimicrobial Agents and Chemotherapy, Dec. 2011, pp. 5646-5653, vol. 55, No. 12.
Dong Joo Seo, et al., "Comparison of the antiviral activity of flavonoids against murine norovirus and feline calicivirus", Food Control, Jul. 17, 2015, pp. 25-30, vol. 60.
International Search Report for PCT/JP2016/087863 dated Mar. 21, 2017 [PCT/ISA/210].

* cited by examiner

ANTI-NOROVIRUS COMPOSITION AND UTILIZATION THEREOF

CROSS REFERENCE TO RELATED APPLICATIONS

This application is a National Stage of International Application No. PCT/JP2016/087863, filed on Dec. 20, 2016, which claims priority from Japanese Patent Application No. 2015-253661, filed on Dec. 25, 2015.

TECHNICAL FIELD

The present invention relates to a composition having an excellent anti-norovirus effect, use of a theaflavin compound for preparation thereof, and a method for preventing infection with a norovirus using the theaflavin compound.

BACKGROUND ART

A norovirus categorized in species Norwalk virus, genus Norovirus, family Caliciviridae, enters into a human body by oral infection through fingers, foods, cookware and the like, and grows in an intestinal tract cell to cause a symptom such as abdominal pain, diarrhea, vomiting and fever. In addition, secondary infectivity by a patient's own vomit or excrement is significantly strong, and therefore large-scale mass infection has successively occurred in recent years. Neither a vaccine nor a therapeutic drug against the norovirus is provided, and treatment with sodium hypochlorite or heating has been so far recommended, but it is far from appropriate to directly act the pharmaceuticals on the human body or the cookware or even the foods.

Patent Literature 1 below discloses an anti-norovirus agent that contains an extract of plant of genus *Diospyros* containing tannin as an active ingredient to such a problem.

RELATED ART

Patent Literature

[Patent Literature 1] JP-B-5092145

Problems to Be Solved by the Invention

However, it has not been reported that a theaflavin compound has an anti-norovirus effect.

In view of the conventional technology described above, an object of the present invention is to provide a composition having an excellent anti-norovirus effect, use of a theaflavin compound for preparation thereof, and a method for preventing infection with a norovirus using the theaflavin compound.

Means to Solve the Problems

The present inventors have found that a theaflavin compound has an excellent effect on inactivating a norovirus, and have accomplished the present invention.

First, the present invention provides an anti-norovirus composition, containing a theaflavin compound as an active ingredient for preventing infection with a norovirus.

According to the anti-norovirus composition of the present invention, the composition preferably further contains an alcohol.

According to the anti-norovirus composition of the present invention, the theaflavin compound is preferably one or more members selected from the group consisting of theaflavin, theaflavin-3-O-gallate, theaflavin-3'-O-gallate and theaflavin-3,3'-O-digallate that are derived from tea components.

Second, the present invention provides use of a theaflavin compound for preparation of an anti-norovirus composition containing the theaflavin compound as an active ingredient for preventing infection with a norovirus.

According to the use of the theaflavin compound of the present invention, the anti-norovirus composition preferably further contains an alcohol.

According to the use of the theaflavin compound of the present invention, the theaflavin compound is preferably one or more members selected from the group consisting of theaflavin, theaflavin-3-O-gallate, theaflavin-3'-O-gallate and theaflavin-3,3'-O-digallate that are derived from tea components.

Third, the present invention provides a method for preventing infection with a norovirus, includes applying or administering a theaflavin compound to an object to be prevented from being infected with the norovirus, excluding medical practice.

According to the method for preventing infection with the norovirus of the present invention, the theaflavin compound is preferably applied or administered to the object further with an alcohol.

According to the method for preventing infection with the norovirus of the present invention, the theaflavin compound is preferably one or more members selected from the group consisting of theaflavin, theaflavin-3-O-gallate, theaflavin-3'-O-gallate and theaflavin-3,3'-O-digallate that are derived from tea components.

Advantageous Effects of Invention

The present invention can provide a composition having an excellent anti-norovirus effect, use of a theaflavin compound for preparation thereof, and a method for preventing infection with a norovirus using the theaflavin compound.

MODE FOR CARRYING OUT THE INVENTION

In the present invention, a theaflavin compound is used as an active ingredient in an anti-norovirus composition. The theaflavin compound is known as red-colored polyphenol which is formed during a fermentation process in which tea leaves are processed into black tea. In the tea leaves, catechins are oxidized by polyphenol oxidase activity, peroxidase activity or the like of an enzyme contained in the tea leaves and theaflavin compound is formed. Specific examples of the theaflavin compound include theaflavin, theaflavin-3-O-gallate, theaflavin-3'-O-gallate and theaflavin-3,3'-O-digallate.

As the theaflavin compound, a chemically synthesized product or a compound derived from a natural product such as tea may be used. Specific examples of the chemically synthesized product include a chemically synthesized product synthesized by using catechins such as epicatechin, epigallocatechin, epicatechin-3-gallate, epigallocatechin-3-gallate a raw material and oxidizing the raw material with potassium ferricyanide. Moreover, specific examples of the product derived from the natural product include a tea extract containing a theaflavin compound. It should be noted that the theaflavin compound has accumulated so far a sufficient food experience in which the theaflavin compound is contained as an ingredient contained in the tea extract, and even if a human orally takes the compound, theaflavin compound is a safe chemical. Moreover, as long as an ordinary tea extract is applied, the tea extract has no problem even if the tea extract is used as a food additive.

Hereinafter, specific examples of the tea extract containing the theaflavin compound will be provided.

(Black Tea Extract)

A black tea extract can be obtained by extracting tea leaves (strongly fermented tea) through a black tea fermentation process with a solvent such as water and a water-containing alcohol by stirring the resultant mixture for several minutes to several hours under heating or normal temperature conditions. The black tea extract may be a product having an advanced degree of processing such as purification, concentration and powdering. In order to enhance a content of the theaflavin compound in such a tea extract, specific examples therefor include a method of extending a fermentation time in a black tea fermentation process, and also a method of additionally putting catechins such as epicatechin, epigallocatechin, epicatechin-3-gallate and epigallocatechin-3-gallate to the black tea extract, or adding an enzyme having polyphenol oxidase activity and/or peroxidase activity to the black tea extract, or performing both thereof to cause a reaction for several minutes to several hours under heating or ordinary temperature conditions. As the enzyme having polyphenol oxidase activity and/or peroxidase activity, an enzyme derived from fruits such as apple and banana, a tea leaf extract containing the enzyme, a tea leaves ground product containing the enzyme, and a plant cell culture liquid containing the enzyme or the like can be used. Moreover, as the above-described catechins, catechins derived from tea, such as a catechin preparation derived from tea and a tea extract containing a catechin at a high concentration, and also a catechin preparation derived from any other plant such as cocoa or an extract containing catechin at a high concentration derived from said plant may be used.

(Enzyme-Treated Product of Tea Extract Ingredient)

The enzyme having polyphenol oxidase activity and/or peroxidase activity is added to a tea extract ingredient dissolving or dissolved in a solvent such as water to cause a reaction for several minutes to several hours under heating or ordinary temperature conditions. Thus, a theaflavin compound is produced from catechins contained in the tea extract ingredient. As the enzyme having polyphenol oxidase activity and/or peroxidase activity, an enzyme derived from fruits such as apple and banana, a tea leaf extract containing the enzyme, a tea leaves ground product containing the enzyme, or a plant cell culture liquid containing the enzyme or the like can be used. The enzyme-treated product of the tea extract ingredient thus obtained may be a product having an advanced degree of processing such as purification, concentration and powering.

(Tea Leaf Fermentation Extract)

The tea leaves are ground and prepared in slurry, and when necessary, a solvent such as water is added thereto, and the resultant mixture is fermented for several minutes to several hours under heating or ordinary temperature conditions. Thus, a theaflavin compound is formed from catechins contained in the tea leaves by action of the enzyme having polyphenol oxidase activity and/or peroxidase activity contained in the tea leaves. After the fermentation, when necessary, the resultant material may be subjected to solid-liquid separation, or may be extracted by stirring the resultant material with a solvent such as water, water-containing alcohol or the like for several minutes to several hours under heating or ordinary temperature conditions. The tea leaf fermentation extract thus obtained may be a product having an advanced degree of processing such as purification, concentration and powdering.

(Enzyme-Treated Product of Catechins)

Catechins such as epicatechin, epigallocatechin, epicatechin-3-gallate and epigallocatechin-3-gallate are applied as a raw material, and the enzyme having polyphenol oxidase activity and/or peroxidase activity is added in a solvent such as water to cause a reaction for several minutes to several hours under heating or ordinary temperature conditions. Thus, a theaflavin compound is formed from the catechins such as epicatechin, epigallocatechin, epicatechin-3-gallate and epigallocatechin-3-gallate. As the enzyme having polyphenol oxidase activity and/or peroxidase activity, an enzyme derived from fruits such as apple and banana, a tea leaf extract containing the enzyme, a tea leaves ground product containing the enzyme, a plant cell culture liquid containing the enzyme or the like can be used. Moreover, as the above-described catechins, catechins derived from tea, such as a catechin preparation derived from tea and a tea extract containing a catechin at a high concentration, and also a catechin preparation derived from any other plant such as cocoa or an extract containing a catechin at a high concentration derived from said plant may be used. The enzyme-treated product of catechins thus obtained may be a product having an advanced degree of processing such as purification, concentration and powdering.

It should be noted that, in the present description, the "tea extract" means a material, in addition to the preparation method exemplified above, to cover such a material as long as being an extract containing a theaflavin compound derived from tea in general, which may include an ingredient thereof when applying tea as a raw material or a product derived from catechins being an ingredient thereof.

The tea serving as the raw material of the tea extract described above may be a material obtained from a tea tree of a perennial plant belonging to Theaceae, and is not particularly limited. Specific examples of tea varieties generally cultivated include green tea varieties such as Asatsuyu, Oiwase, Okuhikari, Okumidori, Kanayamidori, Komakage, Samidori, Hatsumomiji, Yamatomidori, Makinoharawase, Minekaori, Meiryoku, Yabukita and Yamanami, oolong tea varieties such as Oolong, Se Zhong, Shui Xian and Tie Guan Yin, and black tea varieties such as Karabeni, Himemidori, Benihikari, Benifuuki, Benifuji and Benihomare. As tea leaves-picking time, any of first picked tea, second picked tea, third picked tea or the like may be applied, and the cultivating countries and areas are not particularly limited.

The anti-norovirus composition of the present invention is capable of preventing infection with the norovirus by using the theaflavin compound being the active ingredient in a manner of bringing the compound into contact with the norovirus to inactivate the norovirus by destroying, declining or suppressing infection ability of the norovirus.

The anti-norovirus composition of the present invention preferably contains the theaflavin compound in an amount of 10 to 100% by mass, further preferably 25 to 100% by mass, and most preferably 40 to 100% by mass, in a solid content. If a content of the theaflavin compound is less than 10% by mass in the solid content, a concentration of the theaflavin compound in contact with the norovirus is decreased, and an effect of preventing infection with the norovirus tends to be reduced. In addition, when the tea extract is used for the theaflavin compound, the tea extract preferably contains the theaflavin compound in an amount of 10 to 100% by mass, further preferably 25 to 100% by mass, and most preferably 40 to 100% by mass in the solid content.

The anti-norovirus composition of the present invention preferably further contains an alcohol together with the theaflavin compound. Thus, the anti-norovirus effect by the theaflavin compound can be further enhanced by the alcohol. Specific examples of the alcohol include ethanol and isopropyl alcohol, and a synthetic alcohol or a fermented alcohol may be used as the alcohol. A content of the alcohol in the anti-norovirus composition is preferably 10 to 95 v/v %, and further preferably 50 to 95 v/v %.

The anti-norovirus composition of the present invention may contain any other raw material or material in addition to the theaflavin compound or the alcohol. For example, as a pharmaceutically advantageous material, when necessary, the anti-norovirus composition can contain a surfactant, a thickening agent, an emulsifying agent, a coloring agent, a flavor, a preservative or the like. Moreover, as a nutritionally advantageous raw material, when necessary, the anti-norovirus composition can contain saccharides such as sugar, fructose and sugar alcohol, a protein, a lipid, and a mineral. Furthermore, when necessary, the anti-norovirus composition can contain a material capable of developing own functionality, such as any other antiviral agent, an antibacterial agent and a bacteriostatic agent.

In order to bring the theaflavin compound being the active ingredient in the anti-norovirus composition of the present invention into contact with the norovirus, for example, such contact can be made by applying or administering the anti-norovirus composition of the present invention or the theaflavin compound contained therein to the object to be prevented from being infected, or the like. A term "applying" herein means spraying, spreading, coating, adding, mixing or fixing the composition to the object being a living body, a non-living body or the like. Moreover, a term "administering" means orally ingesting the composition in the form of an oral agent or the like to the object such as a human or an animal, injecting the composition in the form of an injectionable solution or the like, locally coating the composition onto the epidermis in the form of a cream, a lotion or the like, acting the composition on a body as a whole in the form of a bath salt or the like, acting the composition on a part of the body such as an inside of oral cavity, a limb, hairs on the head, or the like in the form of a mouthwash, a hand soap, a shampoo or the like.

The object to be prevented from being infected, to which the present invention is applied, is not particularly limited. For example, the object may be an object in which a norovirus has resided already, an object in which a norovirus is eyed to possibly reside, an object having a risk of infection, or an object which is desired to be prevented from being infected. When the norovirus has resided already in the object to which the composition is applied or administered, the theaflavin compound can be obviously brought into contact with the norovirus by applying or administering the composition to the object, and even when the norovirus does not reside yet, the theaflavin compound effectively remains in the object to which the composition is applied or administered, and therefore infection with the norovirus, in relation with the one which is attached to the object afterwards or the one which is about to attach to the object, can be prevented by destroying, declining or suppressing the infection ability to inactivate the norovirus. Specific examples thereof include, in a cooking site, cookware such as a kitchen knife, a cutting board, a pan, a cooking range and an oven, a cooking table, a sink, tableware, a dish cloth, a towel, a cooking worker's wear, cooking worker's hands and fingers, face and hairs on the head. In this case, specific examples thereof also include application of the composition to a food material before, during or after cooking, a processed food and a perishable food. Furthermore, specific examples thereof include, in a medical site, a toilet, a floor and a bed in a hospital, a medical worker's wear, a medical worker's hands and fingers, face and hairs on the head. Alternatively, specific examples thereof further include a vomit or excrement of a person visiting a public transportation, a public square, a school or a hospital. Alternatively, specific examples thereof furthermore include orally administering of the compound to a human or animal or fixing the compound to a mask worn by a human for the purpose of preventing infection with a norovirus. Alternatively, specific examples thereof furthermore include incorporation of the compound into foods and drinks such as a gum, a candy, a preventive beverage, and a jelly beverage. However, the object is not limited thereto.

As aspect of a method of application or administration, dose thereof or the like is not particularly limited. To take a typical example, when a surface area can be conceived on the object to be prevented from being infected, the theaflavin compound is applied or administered thereto preferably in an amount of about 0.0001 to 1.0 mg, further preferably in an amount of about 0.001 to 1.0 mg, and most preferably in an amount of about 0.01 to 1.0 mg, per 1 $cm^2$ of the surface area. When the theaflavin compound is applied or administered thereto in an amount less than the above-described range per 1 $cm^2$ of the surface area of the object, a concentration of the theaflavin compound in contact with the norovirus is decreased, and an effect preventing infection with the norovirus tends to be reduced.

Moreover, the theaflavin compound may be applied or administered to the object further with an alcohol. Thus, the anti-norovirus effect by the theaflavin compound can be further enhanced by the alcohol, as described above. A concentration of the alcohol to be used is preferably 10 to 90 v/v %, and further preferably 25 to 90 v/v %.

The anti-norovirus composition of the present invention can take various forms using a suitable substrate, carrier or the like by a publicly-known method. Specific examples thereof include a supplement in the form of a tablet, a granule, a powder, a capsule, a jelly or a drink, a preventive beverage, a disinfectant solution, a gargle liquid, a mouthwash, a dentifrice, an oral spray, a lozenge, an oral disintegrating tablet, a gum, a candy, a jelly beverage and a gummy. Alternatively, the composition does neither exclude a use form such as a food additive and a medicine, nor exclude a use form, targeting people not suffering from diseases, such as so-called foods with function claims (foods whose labels bear, based on scientific evidence, the effect that the specific health effects can be achieved, which contributes to maintaining and promoting health by functional substances, on the containers and packaging) and a use form as the ingredient thereof. Moreover, the anti-norovirus composition of the present invention may be an active ingredient itself, or may be used in combination with any other active ingredient to achieve the effect of preventing infection with the norovirus.

More specifically, specific examples thereof include products as described below.

Disinfectant solution: A product containing an alcohol or bactericide for an antibacterial or anti-virus purpose, and sprayed on hands or skin on a whole body, or applied to a surface of hands in a gel form or liquid form. The product is mainly used for a subject when entering from outside to inside.

Gargle liquid: A product containing a small amount of alcohol or bactericide for an antibacterial or anti-virus purpose, and used for preventing growth of bacteria or viruses in an oral cavity by gargling or rinsing the oral cavity. The product is mainly used for a subject when entering from outside to inside.

Mouthwash: A product used for preventing growth of bacteria or viruses in the oral cavity by washing the mouth, in a manner similar to the above-described gargle liquid.

Oral spray: A product used for preventing growth of bacteria or viruses in the oral cavity by spraying the liquid to a deep side in the oral cavity, in a manner similar to the above-described gargle liquid.

Hand soap: A product containing a bactericide or antimicrobial agent for an antibacterial or anti-virus purpose, and used for preventing growth of bacteria or viruses attached to hands, simultaneously with washing the surface of hands. The product is mainly used for a subject when entering from outside to inside.

Food for preventing infection (gum, candy): A product for preventing infection with bacteria or viruses by an antibacterial ingredient contained in a food by residing the food in the oral cavity for a relatively long period of time.

Beverage or jelly food for preventing infection: A product for preventing infection with bacteria or viruses by an antibacterial ingredient contained in a food by residing the food in the oral cavity for a relatively long period of time.

Nonwoven fabric or mask: A mask provided with a function for an antibacterial or anti-virus purpose. A product fabricated by attaching or bonding an antibacterial material onto a nonwoven fabric and processed into a mask using the nonwoven fabric. Infection with bacteria or viruses is prevented by wearing the mask.

EXAMPLES

Hereinafter, the present invention will be described in further detail by way of Examples, but the Examples do not limit the scope of the present invention at all.

<Production Example 1> Theaflavin-Containing Crude Extract No. 1

Into 400 mL of water, 0.3 g of catechin preparation derived from green tea (catechin content: 90% or more, trade name: "Sunphenon 90", made by Taiyo Kagaku Co., Ltd.) was dissolved. Separately, 100 mL of water was added to 3 g of tea leaves, and ground to obtain a tea ground product. The above-described catechin solution was combined with the tea ground product, and reacted at 30 to 35° C. for three hours. The reaction liquid after the reaction was purified by passing through a synthetic adsorbent "Sepabeads SP-700" (trade name; made by Mitsubishi Chemical Corporation), and powdered by freeze drying to obtain 0.1 g of theaflavin-containing crude extract. When the extract was analyzed by HPLC, 6% by mass of theaflavin, 14% by mass of theaflavin-3-O-gallate, 4% by mass of theaflavin-3'-O-gallate and 18% by mass of theaflavin-3,3'-O-digallate were contained in the theaflavin-containing crude extract, a total content of the theaflavin compound was 42% by mass.

<Production Example 2> Theaflavin-Containing Purified Extract

Into 20% acetone, 4 g of the theaflavin-containing crude extract obtained by the same preparation as in Production Example 1 was dissolved, and the resultant solution was fractionated by being applied to gel filtration column "Sephadex LH-20" (trade name; made by GE Healthcare Japan Ltd.) swollen also with 20% acetone to obtain a theaflavin-containing extract. The theaflavin-containing extract was powdered by freeze drying to obtain 1.5 g of theaflavin-containing purified extract. When the extract was analyzed by HPLC, 16% by mass of theaflavin, 27% by mass of theaflavin-3-O-gallate, 7% by mass of theaflavin-3'-O-gallate, and 40% by mass of theaflavin-3,3'-O-digallate were contained the theaflavin-containing purified extract, and a total content of the theaflavin compound was 90% by mass.

<Production Example 3> Theaflavin-Containing Crude Extract No. 2

To 50 g of tea leaves for green tea, 400 mL of hot water was added, and the resultant mixture was stirred, and then subjected to solid-liquid separation to obtain a green tea extract. Separately, 100 g of water was added to 3 g of tea leaves for green tea, and ground to obtain a tea ground product. The above-described green tea extract was combined with the tea ground product, and was reacted at 30 to 35° C. for three hours. The reaction liquid after the reaction was purified by passing through a synthetic adsorbent "Sepabeads SP-700" (trade name, made by Mitsubishi Chemical Corporation), and powdered by freeze drying to obtain 0.1 g of a theaflavin-containing crude extract. When the extract was analyzed by HPLC, 4% by mass of theaflavin, 10% by mass of theaflavin-3-O-gallate, 3% by mass of theaflavin-3'-O-gallate and 14% by mass of theaflavin-3,3'-O-digallate were contained in the theaflavin-containing crude extract, and a total content of the theaflavin compound was 31% by mass.

<Test Example 1> Antiviral Activity Against Murine Norovirus

[Test Method]
(1) Virus
Murine norovirus strain S7 was obtained and used.
(2) Cell
A RAW 264.7 cell being a cell line derived from a murine macrophage (ATCC (American Type Culture Collection) TIB-71) was obtained and used.
(3) Test Sample
The theaflavin-containing purified extract (hereinafter referred to as "theaflavin purified product") obtained in Production Example 2 was used as a test sample. Moreover, as a test sample for comparison, tannic acid having nonspecific protein binding ability and also reported as to effectiveness against a norovirus, and products A and B being the existing anti-virus products were used.
(4) Preparation of Sample for Anti-Virus Test
The theaflavin purified product was dissolved in dimethyl sulfoxide to be 71.7 mg/mL, and the resultant material was used in the test described below.
Tannic acid was dissolved in dimethyl sulfoxide to be 169.9 mg/mL, and the resultant material was used in the test described below.
(5) Preparation of Cell for Anti-Virus Test
A RAW 264.7 cell was monolayer cultured in a well of a 96-well plate, and washed twice with PBS (Phosphate Buffered Saline), and 200 μL of cell maintenance medium (2% fetal bovine serum-containing Dulbecco's Modified Eagle Medium (DMEM)) was added, and the resultant material was used in the test described below.

(6) Anti-Virus Test

For each test sample, a concentration was adjusted as described below, and the resultant material was applied as a test solution.

For the theaflavin purified product, the sample for anti-virus test prepared in the item (4) described above was diluted with a 25% ethanol-added serum-free DMEM medium to be 1.5 mg/mL in a concentration of the theaflavin purified product, and the resultant material was applied as a test solution.

For tannic acid, the sample for the anti-virus test prepared in the item (4) described above was diluted with a 25% ethanol-added serum-free DMEM medium to be 1.5 mg/mL in a concentration of tannic acid, and the resultant material was applied as a test solution.

For the product A, a stock solution was directly applied as a test solution.

For the product B, a stock solution was directly applied as a test solution.

Then, 5 µL of a murine norovirus solution and 45 µL of the test solution were mixed, and reacted for 60 minutes.

To the reaction liquid, 450 µL of serum-free DMEM medium was added to stop the reaction.

The resultant material was centrifuged with a centrifugal filter (fractionation molecular weight: 100 K) (room temperature, 20,000×g, 1 min, continued to addition of 450 µL of medium, further continued to room temperature, 20,000×g, 1 min) to collect a virus.

The collected virus was diluted with 300 µL of serum-free DMEM medium, and the resultant material was applied as a virus test solution, and five-fold serial dilutions were prepared using the serum-free DMEM medium for the virus test solution.

To a supernatant of the cell for the anti-virus test arranged in the item (5) described above, the diluted virus test solution was added by 50 µL (3 wells for each concentration), and the resultant material was cultured at 37° C. for three days in the presence of 5% $CO_2$.

A cytopathic effect (CPE) was observed and a 50% tissue culture infectious dose ($TCID_{50}$) being an indicator of a virus infectivity titer was calculated by the Behrens-Karber method. Moreover, a virus test solution untreated with the test sample was prepared in the same procedure, and the cytopathic effect was also observed on a cell to which the virus test solution was inoculated to determine a 50% tissue culture infectious dose (log ($TCID_{50}$ value)). A reduction value of the virus infectivity titer by the test sample was calculated according to the formula (1) described below.

$$\text{Reduction value of virus infectivity titer} = (\log(TCID_{50} \text{ value of untreated group}) - (\log(TCID_{50} \text{ value of treated group})) \quad (1)$$

[Results]

Figure 1:
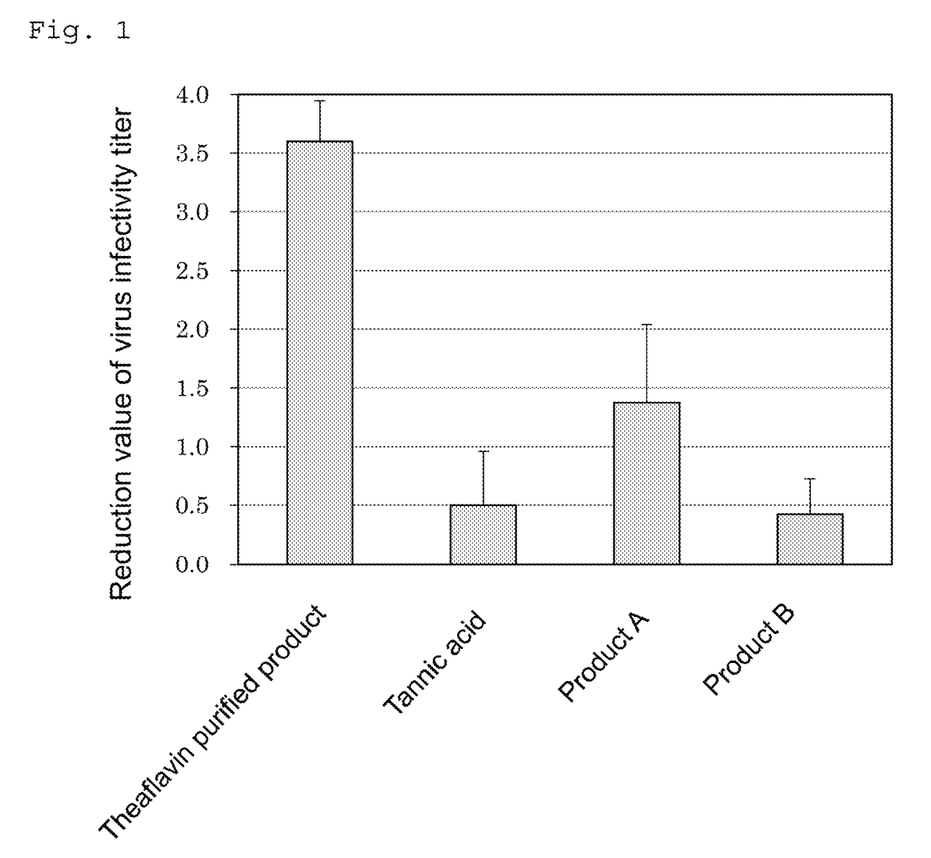
FIG. 1 is a figure showing the results of Test Example 1.

The results are shown in Table 1 and FIG. 1.

TABLE 1

| Test sample | Reduction value of virus infectivity titer Average | SD | Effectiveness (Reduction value: 2 or more) |
|---|---|---|---|
| Theaflavin purified product | 3.6 | 0.3 | Good |
| Tannic acid | 0.5 | 0.5 | Poor |
| Product A | 1.4 | 0.7 | Poor |
| Product B | 0.4 | 0.3 | Poor |

Table 1 and FIG. 1 show that the theaflavin purified product is significantly superior, in an effect of inactivating infection ability of the murine norovirus, to tannic acid and the products A and B being the existing anti-virus products.

<Test Example 2> Anti-Virus Activity Against Feline Calicivirus No. 1

[Test Method]
(1) Virus

Feline calicivirus strain F9 was obtained and used as a surrogate virus for the norovirus.

(2) Cell

A Crandell Rees feline kidney (CRFK) cell (ATCC CCL-94) being a cell line derived from a feline kidney cell was obtained and used.

(3) Test Sample

The theaflavin-containing purified extract (hereinafter referred to as "theaflavin purified product") obtained in Production Example 2 was used as a test sample.

(4) Preparation of Sample for Anti-Virus Test

The theaflavin purified product was dissolved in dimethyl sulfoxide to be 71.7 mg/mL, and the resultant material was used in the test described below.

(5) Preparation of Cell for Anti-Virus Test

A CRFK cell was monolayer cultured in a well of a 96-well plate, and washed twice with PBS and 200 µL of cell maintenance medium (2% fetal bovine serum-containing Minimum Essential Medium (MEM)) was added, and the resultant material was used in the test described below.

(6) Anti-Virus Test

As a test sample, the sample for the anti-virus test (high concentration) prepared in the item (4) described above was diluted with a 25% ethanol-added serum-free Eagle's MEM medium to be 1.8 mg/mL in a concentration of the theaflavin purified product, and the resultant material was applied as a test solution.

Then, 5 µL of a feline calicivirus solution and 45 µL of the test solution were mixed, and reacted for 5 minutes, 30 minutes or 60 minutes.

To the reaction liquid, 450 µL of serum-free Eagle's MEM medium was added to stop the reaction.

The resultant solution was centrifuged with a centrifugal filter (fractionation molecular weight: 100 K) (room temperature, 20,000×g, 1 min, continued to addition of 450 µL of medium, further continued to room temperature, 20,000×g, 1 min) to collect a virus.

The collected virus was diluted with 300 µL of serum-free Eagle's MEM medium, and the resultant material was applied as a virus test solution, and five-fold serial dilutions were prepared using the serum-free Eagle's MEM medium for the virus test solution.

To a supernatant of the cell for the anti-virus test arranged in the item (5) described above, the diluted virus test solution was added by 50 µL (3 wells for each concentration), and the resultant material was cultured at 37° C. for three days in the presence of 5% $CO_2$.

A reduction value of a virus infectivity titer by the test sample was calculated in the same manner as in Test Example 1.

[Results]

Figure 2:
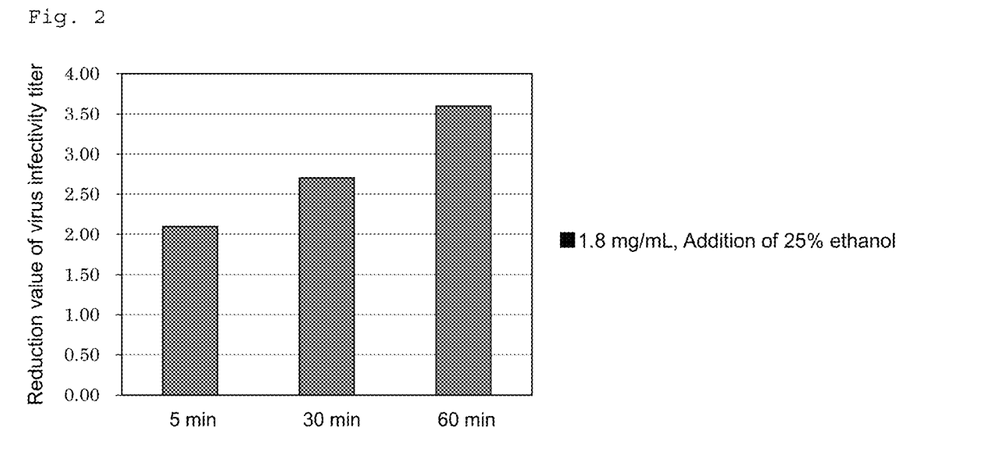
FIG. 2 is a figure showing the results of Test Example 2.

The results are shown in Table 2 and in FIG. 2.

TABLE 2

| | 1.8 mg/mL, addition of 25% ethanol | |
|---|---|---|
| Reaction Time | Average of reduction value of virus infectivity titer | Effectiveness (Reduction value: 2 or more) |
| 5 min | 2.1 | Good |
| 30 min | 2.7 | Good |
| 60 min | 3.6 | Good |

Table 2 and FIG. 2 show that infection ability of feline calicivirus (surrogate for norovirus) was inactivated by the theaflavin purified product. The effect was dependent on a treatment time with the theaflavin purified product.

<Test Example 3> Anti-Virus Activity Against Feline Calicivirus No. 2

[Test Method]

Anti-virus activity of the test sample against feline calicivirus was examined in the same manner as in Test Example 2 except that "(4) Preparation of sample for anti-virus test" and "(6) Anti-virus test" were conducted as described below.

(4) Preparation of Sample for Anti-Virus Test

A theaflavin purified product was dissolved in dimethyl sulfoxide to be 0.717 mg/mL (low concentration), 7.17 mg/mL (medium concentration) and 71.7 mg/mL (high concentration), and the resultant material was used in the test described below.

(6) Anti-Virus Test

As a test sample, (A): the sample for the anti-virus test (low concentration) prepared in the item (4) described above was diluted with a serum-free Eagle's MEM medium without adding ethanol or a 25% ethanol-added serum-free Eagle's MEM medium to be 0.018 mg/mL in a concentration of the theaflavin purified product; (B) the sample for the anti-virus test (medium concentration) prepared in the item (4) described above was diluted with the serum-free Eagle's MEM medium without adding ethanol or the 25% ethanol-added serum-free Eagle's MEM medium to be 0.18 mg/mL in the concentration of the theaflavin purified product; and (C): the sample for the anti-virus test (high concentration) prepared in the item (4) described above was diluted with the serum-free Eagle's MEM medium without adding ethanol or the 25% ethanol-added serum-free Eagle's MEM medium to be 1.8 mg/mL in the concentration of the theaflavin purified product, and each was adjusted to be the same in the concentration of dimethyl sulfoxide, and the resultant material was applied as a test solution.

Then, 5 μL of a feline calicivirus solution and 45 μL of the test solution were mixed, and reacted for 60 minutes.

To the reaction liquid, 450 μL of serum-free Eagle's MEM medium was added to stop the reaction.

The resultant material was centrifuged with a centrifugal filter (fractionation molecular weight: 100 K) (room temperature, 20,000×g, 1 min, continued to addition of 450 μL of medium, further continued to room temperature, 20,000× g, 1 min) to collect a virus.

The collected virus was diluted with 300 μL of serum-free Eagle's MEM medium, and the resultant material was applied as a virus test solution, and five-fold serial dilutions were prepared using the serum-free Eagle's MEM medium for the virus test solution.

To a supernatant of the cell for the anti-virus test arranged in the item (5) described above, the diluted virus test solution was added by 50 μL (3 wells for each concentration), and the resultant material was cultured at 37° C. for three days in the presence of 5% $CO_2$.

A reduction value of a virus infectivity titer by the test sample and/or ethanol was calculated in the same manner as in Test Example 1.

[Results]

Figure 3:
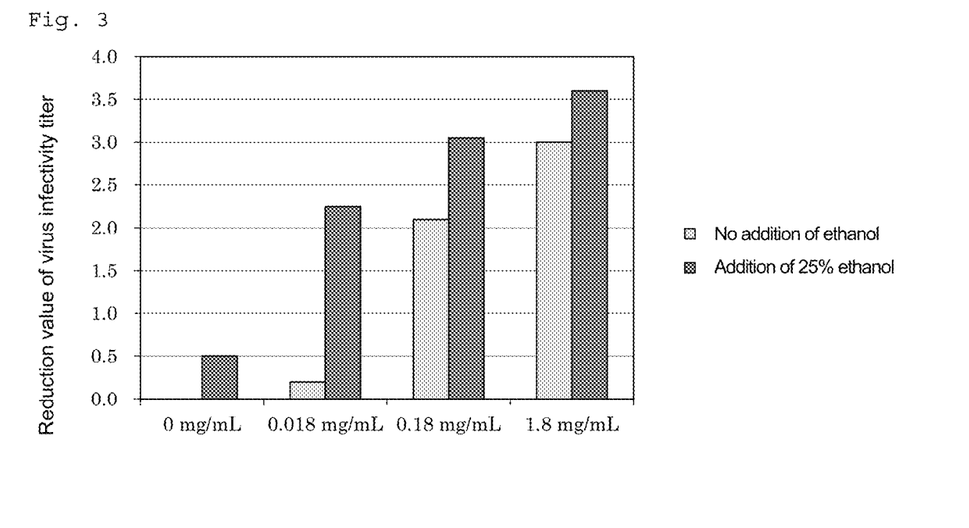
FIG. 3 is a figure showing the results of Test Example 3.

The results are shown in Table 3 and FIG. 3.

TABLE 3

| | No addition of ethanol | | Addition of 25% ethanol | |
|---|---|---|---|---|
| Concentration of theaflavin | Average reduction value of virus infectivity titer | Effectiveness (Reduction value: 2 or more) | Average reduction value of virus infectivity titer | Effectiveness (Reduction value: 2 or more) |
| No addition | — | — | 0.5 | Poor |
| 0.018 mg/mL | 0.2 | Poor | 2.3 | Good |
| 0.18 mg/mL | 2.1 | Good | 3.1 | Good |
| 1.8 mg/mL | 3.0 | Good | 3.6 | Good |

Table 3 and FIG. 3 show that infection ability of feline calicivirus (surrogate for norovirus) was inactivated by the theaflavin purified product. The effect was dose-dependent. In particular, when a concentration of addition is 0.018 mg/mL, the reduction value of the virus infectivity titer upon using in combination with 25% ethanol was more than 2, in comparison of 0.2 in the reduction value of the virus infectivity titer upon using no ethanol. On the other hand, the reduction value of the virus infectivity titer upon treating the sample with only 25% ethanol was 0.5, and it became clear that an anti-norovirus effect was synergistically improved by use in combination with the theaflavin purified product and ethanol.

[Example 1] Disinfectant Solution for Anti-Norovirus

Raw materials were mixed in a formulation in Table 4 below, and the resultant mixture was stirred to obtain a disinfectant solution for an anti-norovirus.

TABLE 4

| [Disinfectant solution for anti-norovirus] | |
|---|---|
| Raw material | % by mass |
| Theaflavin purified product (90%) | 0.18 |
| Ethanol | 75 |
| Citric acid | 1.5 |
| Trisodium citrate | 0.5 |
| Glycerol monocaprate | 0.5 |
| Vitamin C | 0.5 |
| Water | Balance |
| (Total amount) | 100 |

[Example 2] Mouthwash for Anti-Norovirus

Raw materials were mixed in a formulation in Table 5 below, and the resultant mixture was stirred to obtain a mouthwash for anti-norovirus.

TABLE 5

[Mouthwash for anti-norovirus]

| Raw material | % by mass |
|---|---|
| Theaflavin purified product (90%) | 0.18 |
| Ethanol | 25 |
| Chlorohexidine hydrochloride | 0.05 |
| Sodium lauryl sulfate | 5 |
| Methylparaben | 0.1 |
| Vitamin C | 0.5 |
| Water | Balance |
| (Total amount) | 100 |

[Example 3] Hand Soap for Anti-Norovirus

Raw materials were mixed in a formulation in Table 6 below, and the resultant mixture was stirred to obtain a hand soap for anti-norovirus.

TABLE 6

[Hand soap for anti-norovirus]

| Raw material | % by mass |
|---|---|
| Theaflavin purified product (90%) | 0.18 |
| Iso-Propylmethyl phenol | 0.1 |
| Lauryl glucoside | 7.5 |
| Glycerol | 15 |
| Citric Acid | 1.0 |
| Glycerol monocaprate | 0.3 |
| Water | Balance |
| (Total amount) | 100 |

[Example 4] Gum for Anti-Norovirus

A gum for anti-norovirus was obtained in a formulation of raw materials shown in Table 7 below according to an ordinary method.

TABLE 7

[Gum for anti-norovirus]

| Raw material | % by mass |
|---|---|
| Theaflavin purified product (90%) | 0.1 |
| Gum base | 20 |
| Powdered sugar | 60 |
| Crystalline glucose | 18.9 |
| Flavor | 1.0 |
| (Total amount) | 100 |

[Example 5] Hard Candy for Anti-Norovirus

A hard candy for anti-norovirus was obtained in a formulation of raw materials shown in Table 8 below according to an ordinary method.

TABLE 8

[Hard candy for anti-norovirus]

| Raw material | % by mass |
|---|---|
| Theaflavin purified product (90%) | 0.1 |
| Granulated sugar | 53.8 |
| Starch syrup | 40 |
| Acids | 0.7 |
| Flavor | 0.4 |
| Water | 5 |
| (Total amount) | 100 |

[Example 6] Mask for Anti-Norovirus

The theaflavin-containing crude extract (content of theaflavin compound: 42% by mass) obtained in Production Example 1 was attached to a nonwoven fabric to be 0.24 g/m² per unit area to obtain a theaflavin-attached nonwoven fabric. A mask was formed using the nonwoven fabric to obtain a mask for anti-norovirus.

What is claimed is:

1. A method for suppressing infection with a norovirus, comprising applying or administering an anti-norovirus composition including theaflavin compounds to an object or subject, and suppressing infection of the object or subject with the norovirus, wherein the theaflavin compounds consist of theaflavin, theaflavin-3-O-gallate, theaflavin-3'-O-gallate and theaflavin-3,3'-O-digallate, and wherein the anti-norovirus composition contains the theaflavin compounds in an effective amount of 40 to 100% by mass to suppress infection with the norovirus.

2. The method according to claim 1, wherein the anti-norovirus composition further contains an alcohol.

3. A method for reducing infectivity with a norovirus, comprising applying anti-norovirus composition including theaflavin compounds to an object, excluding living body and biological materials, and reducing the infectivity of the norovirus with the object, wherein the isolated theaflavin compounds consist of theaflavin, theaflavin-3-O-gallate, theaflavin-3'-O-gallate and theaflavin-3,3'-O-digallate, and wherein the anti-norovirus composition contains the theaflavin compounds in an effective amount of 40 to 100% by mass in an effective amount to suppress infection with the norovirus.

4. The method according to claim 3, wherein the anti-norovirus composition further contains an alcohol.

* * * * *